United States Patent
Laskar et al.

(10) Patent No.: US 12,414,517 B2
(45) Date of Patent: Sep. 16, 2025

(54) WHEAT VARIETY 6PASS54B

(71) Applicant: PIONEER HI-BRED INTERNATIONAL, INC., Johnston, IA (US)

(72) Inventors: William Joseph Laskar, Tipton, IN (US); Cristiano Lemes Da Silva, Westfield, IN (US); Kyle Jay Lively, Tipton, IN (US); Gregory Charles Marshall, Arcadia, IN (US); James Joseph Uphaus, Glandorf, OH (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 572 days.

(21) Appl. No.: 17/455,458

(22) Filed: Nov. 18, 2021

(65) Prior Publication Data

US 2023/0148522 A1    May 18, 2023

(51) Int. Cl.
*A01H 6/46* (2018.01)
*A01H 5/10* (2018.01)

(52) U.S. Cl.
CPC ............. *A01H 6/4678* (2018.05); *A01H 5/10* (2013.01)

(58) Field of Classification Search
None
See application file for complete search history.

(56) References Cited

U.S. PATENT DOCUMENTS 9,474,244 B1 * 10/2016 Laskar ..................... A01H 5/10

* cited by examiner

*Primary Examiner* — Anne Kubelik

(57) ABSTRACT

A wheat variety designated 6PASS54B, the plants and seeds of wheat variety 6PASS54B, methods for producing a wheat plant produced by crossing the variety 6PASS54B with another wheat plant, and hybrid wheat seeds and plants produced by crossing the variety 6PASS54B with another wheat line or plant, and the creation of variants by backcrossing, mutagenesis or transformation of variety 6PASS54B are disclosed. Methods for producing other wheat varieties or breeding lines derived from wheat variety 6PASS54B and to wheat varieties or breeding lines produced by those methods are also provided.

20 Claims, No Drawings

WHEAT VARIETY 6PASS54B

FIELD OF INVENTION

This invention is in the field of wheat (*Triticum aestivum* L.) breeding, specifically relating to a wheat variety designated 6PASS54B.

BACKGROUND OF INVENTION

There are numerous steps involving significant intervention in the development of any novel, desirable plant germ plasm. The goal is to combine in a single variety an improved combination of desirable traits from the parental germ plasm. These traits may include, but are not limited to, higher seed yield, resistance to diseases and/or insects, tolerance to drought and/or heat, altered milling properties, abiotic stress tolerance, improvements in compositional traits, and better agronomic characteristics.

Wheat is grown worldwide and is the most widely adapted cereal. There are five main wheat market classes. They include the four common wheat (*Triticum aestivum* L.) classes: hard red winter, hard red spring, soft red winter, and white (hard and soft). The fifth class is durum (*Triticum turgidum* L.). Common wheats are used in a variety of food products such as bread, cookies, cakes, crackers, and noodles. In general, the hard wheat classes are milled into flour used for breads and the soft wheat classes are milled into flour used for pastries and crackers. Wheat starch is also used in the paper industries, as laundry starches, and in other products.

SUMMARY OF THE INVENTION

Seeds of the wheat variety 6PASS54B are provided. Also provided are plants produced by growing the seed of the wheat variety 6PASS54B, as well as the derivatives of such plants. Further provided are plant parts, including cells, plant protoplasts, plant cells of a tissue culture from which wheat plants can be regenerated, plant calli, plant clumps, and plant cells that are intact in plants or parts of plants, such as leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells, and the like.

In a further aspect, a composition comprising a seed of wheat variety 6PASS54B comprised in plant seed growth media is provided. The plant seed growth media can be, for example, a soil or synthetic cultivation medium. The growth medium may be comprised in a container or may, for example, be soil in a field. Plant seed growth media are well known to those of skill in the art and include, but are in no way limited to, soil or synthetic cultivation medium. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media include those known in the art and may, for example, comprise polymers or hydrogels. Examples of such compositions are described in U.S. Pat. No. 4,241,537.

A tissue culture of regenerable cells of the wheat variety 6PASS54B is provided, as well as plants and plant parts regenerated therefrom, wherein the regenerated wheat plant is capable of expressing all the physiological and morphological characteristics of a plant grown from the wheat seed designated 6PASS54B.

A wheat plant comprising a locus conversion or single locus conversion of the wheat variety 6PASS54B, wherein the wheat plant is otherwise capable of expressing all the physiological and morphological, or phenotypic, characteristics of the wheat variety 6PASS54B is provided. The locus conversion may comprise, for example, a transgenic gene which has been introduced by genetic transformation into the wheat variety 6PASS54B or a progenitor thereof. The locus conversion may, for example, comprise a dominant or recessive allele or a genetic modification introduced by manipulation of the plant genome. The locus conversion may confer potentially any trait upon the converted plant, including, but not limited to, herbicide resistance, insect resistance, resistance to bacterial, fungal, or viral disease, male fertility or sterility, abiotic stress, altered phosphorus content, altered antioxidants, altered essential amino acids, and altered nutritional quality, such as altered starch, sugars, non-digestible carbohydrate, protein, oil or fatty acids. The altered trait can be compared to a wheat variety 6PASS54B not comprising the locus conversion.

Wheat plants are provided which comprise a transgene or genetic modification and which were produced by transforming or modifying the plant, plant part, seed or cell of wheat variety 6PASS54B, or which had the transgene or the genetic modification introgressed through back-crossing.

Methods for producing a wheat plant are provided in which plant breeding techniques are applied to a wheat plant grown from seed of wheat variety 6PASS54B comprising a locus conversion, or to a plant grown from seed of a cross of such a wheat plant to a different wheat plant.

First generation (F1) hybrid wheat seed produced by crossing a plant of the wheat variety 6PASS54B to a second wheat plant are provided. Also provided are the F1 hybrid wheat plants grown from the hybrid seed produced by crossing the wheat variety 6PASS54B to a second wheat plant. Still further provided are the seeds of an F1 hybrid plant produced with the wheat variety 6PASS54B as one parent, the second generation (F2) hybrid wheat plant grown from the seed of the F1 hybrid plant, and the seeds of the F2 hybrid plant.

Methods of producing wheat seeds are provided which comprise crossing a plant of the wheat variety 6PASS54B to any second wheat plant, including itself or another plant of the variety 6PASS54B. For example, the method of crossing can comprise the steps of: (a) planting seeds of the wheat variety 6PASS54B; (b) cultivating wheat plants resulting from said seeds until said plants bear flowers; (c) allowing fertilization of the flowers of said plants; and (d) harvesting seeds produced from said plants.

A method of producing hybrid wheat seeds is provided which comprises crossing the wheat variety 6PASS54B to a second, distinct wheat plant that is nonisogenic to the wheat variety 6PASS54B. For example, the crossing can comprise the steps of: (a) planting seeds of wheat variety 6PASS54B and a second, distinct wheat plant, (b) cultivating the wheat plants grown from the seeds until the plants bear flowers; (c) cross pollinating a flower on one of the two plants with the pollen of the other plant, and (d) harvesting the seeds resulting from the cross pollinating.

A method for developing a wheat plant in a wheat breeding program is provided comprising: (a) obtaining or providing a wheat plant, or its parts, of the variety 6PASS54B; and (b) employing said plant or parts as a source of breeding material in a plant breeding program such as using plant breeding techniques. In the method, the plant breeding techniques may be selected, for example, from recurrent selection, mass selection, bulk selection, backcrossing, pedigree breeding, genetic marker-assisted selection and genetic transformation. The wheat plant of variety 6PASS54B may be used as the male or female parent.

A method of producing a wheat plant derived from the wheat variety 6PASS54B is provided, the method comprising the steps of: (a) preparing a progeny plant derived from wheat variety 6PASS54B by crossing a plant of the wheat variety 6PASS54B with a second wheat plant; and (b) crossing the progeny plant with itself or a second plant to produce a progeny plant of a subsequent generation which is derived from a plant of the wheat variety 6PASS54B. Optionally, the method may further comprise: (c) crossing the progeny plant of a subsequent generation with itself or a second plant; and (d) repeating steps (b) and (c) for at least, for example 2, 3, 4 or more additional generations to produce an inbred wheat plant derived from the wheat variety 6PASS54B. Also provided is a plant produced by this and other methods described herein.

A method of producing a wheat plant derived from the wheat variety 6PASS54B can, for example, further comprise: (a) crossing the wheat variety 6PASS54B-derived wheat plant with itself or another wheat plant to yield additional wheat variety 6PASS54B-derived progeny wheat seed; (b) growing the progeny wheat seed of step (a) under plant growth conditions to yield additional wheat variety 6PASS54B-derived wheat plants; and (c) repeating the crossing and growing steps of (a) and (b) to generate further wheat variety 6PASS54B-derived wheat plants. Steps (a) and (b) can be repeated if desired at least 1, 2, 3, 4, or 5 or more times. Also provided is a wheat plant produced by this and other methods described herein.

Methods for producing double haploid wheat plants from wheat variety 6PASS54B are provided. For example, a wheat plant produced by growing a seed of the cross of wheat variety 6PASS54B with a different wheat plant or plant part can be crossed with another plant to form haploid cells. The chromosomes of the haploid cells can be doubled to form double haploid cells which are grown into a double haploid wheat plant or plant part. Haploid seed generated from a cross of a wheat plant disclosed herein with a different wheat plant can be doubled to produce a wheat plant having doubled haploid chromosomes.

Methods for cleaning, conditioning, or applying a seed treatment to the seed of wheat variety 6PASS54B are provided.

Methods of milling the seed of wheat variety 6PASS54B and the flour produced from such milling are provided. The flour may include a cell of wheat variety 6PASS54B.

DETAILED DESCRIPTION

The present invention relates to a new and distinctive wheat (*Triticum aestivum* L.) variety designated 6PASS54B, its seeds, plants, plant parts and hybrids. Variety 6PASS54B represents a significant advancement in elite germ plasm.

Also provided are methods for making 6PASS54B that comprise crossing wheat variety 6PASS54B with another wheat plant and processes for making a wheat plant containing in its genetic material one or more traits introgressed into 6PASS54B through backcross conversion and/or transformation or genetic modification, and to the wheat seed, plant and plant parts produced thereby. Variants of wheat 6PASS54B created by mutagenesis or transformation, such as genetic modification, as well as a hybrid wheat seed, plant or plant part produced by crossing the variety 6PASS54B or a locus conversion of 6PASS54B with another wheat variety are also provided.

Wheat variety 6PASS54B has shown uniformity and stability for all traits, as described in the variety description information provided herein. It has been self-pollinated a sufficient number of generations, with careful attention to uniformity of plant type to ensure homozygosity and phenotypic stability. The line has been increased with continued observation for uniformity. No variant traits have been observed or are expected in 6PASS54B, as described, for example, in Table 2 at the end of this section.

Field crops are bred through techniques that take advantage of the plant's method of pollination, such as self-pollination, sib-pollination or cross-pollination. As used herein, the term cross-pollination includes pollination with pollen from a flower on a different plant from a different family or line and does not include self-pollination or sib-pollination. Wheat plants (*Triticum aestivum* L.), are recognized to be naturally self-pollinated plants which, while capable of undergoing cross-pollination, rarely do so in nature. Thus intervention for control of pollination is needed for the establishment of superior varieties.

Provided are methods of producing progeny with a new combination of genetic traits by cross pollinating one wheat plant with another by emasculating flowers of a designated female plant and pollinating the female parent with pollen from the designated male parent. Suitable methods of cross-pollination of wheat plants are described, for example, in U.S. Pat. No. 8,809,654, which is herein incorporated by reference, but other methods can be used, or modified, as is known to those skilled in the art.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci.

Choice of breeding or selection methods depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection can be based on mean values obtained from replicated evaluations of families of related plants. Popular selection methods which can be used include pedigree selection, modified pedigree selection, mass selection, and recurrent selection.

The complexity of inheritance influences choice of the breeding method. For example, pedigree breeding, backcross breeding, single seed descent, and bulk breeding, which are each described in U.S. Pat. No. 8,809,654 (incorporated herein by reference), can be used. Each wheat breeding program may include a periodic, objective evaluation of the efficiency of the breeding procedure. Evaluation criteria vary depending on the goal and objectives, but may include gain from selection per year based on comparisons to an appropriate standard, overall value of the advanced breeding lines, and number of successful varieties produced per unit of input (e.g., per year, per dollar expended, etc.).

Various recurrent selection techniques can be used to improve quantitatively inherited traits controlled by numerous genes. The use of recurrent selection in self-pollinating crops depends on the ease of pollination and the number of hybrid offspring from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and selfed to create new varieties.

Wheat variety 6PASS54B can be used as the female or the male parent in biparental crosses in order to develop new and valuable wheat varieties or hybrids. Wheat normally self-pollinates in nature. Cross pollination of one wheat plant with another to produce progeny with a new combination of genetic traits, can be carried out according to methods known to those skilled in the art. Wheat cross-pollination is achieved by emasculating flowers of a designated female plant and pollinating the female parent with pollen from the designated male parent. Methods of cross-pollinating wheat plants for use in selection and advancement are described, for example in U.S. Pat. No. 9,282,712, the disclosure of which is incorporated herein by reference in its entirety.

Plant breeding methods may include analysis, comparison and characterization of the plant genome and the use of molecular markers, including techniques such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), Single Nucleotide Polymorphisms (SNPs) and Quantitative Trait Loci (QTL) mapping.

Molecular markers can also be used during the breeding process for the selection of qualitative traits. For example, markers closely linked to alleles or markers containing sequences within the actual alleles of interest can be used to select plants that contain the alleles of interest during a crossing or backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program.

The production of double haploids can also be used for the development of homozygous lines in the breeding program and in the production of, for example, hybrid wheat using variety 6PASS54B. Double haploids are produced by the doubling of a set of chromosomes (1 N) from a heterozygous plant to produce a completely homozygous individual. This can be advantageous because the process omits the generations of selfing needed to obtain a homozygous plant from a heterozygous source. Hybrid wheat can be produced, for example, in methods utilizing cytoplasmic male sterility, nuclear genetic male sterility, chemicals, genetic modification or a combination thereof.

Wheat variety 6PASS54B can be crossed with one or more parental lines, followed by repeated selfing and selection, producing many new genetic combinations. Selected germ plasm can be grown under unique and different geographical, climatic and soil conditions with further selections being made during and at the end of the growing season.

Wheat varieties that are highly homogeneous, homozygous and reproducible are useful as commercial varieties. There are many analytical methods, such as those described herein, which can be used to determine the homozygotic stability, phenotypic stability, and identity of these varieties produced or derived from variety 6PASS54B. Gel electrophoresis is particularly useful in wheat. Wheat variety identification can occur, for example, through electrophoresis of gliadin, glutenin, albumin and globulin, and total protein extracts.

Disclosed are plant breeding methods in which plant populations as well as individual plants are evaluated for general health, agronomics, and stability at one or more stages. These evaluations can include, but are not limited to, one or more of the following characteristics: plant architecture traits such as seedling coleoptile length, coleoptile color (presence of anthocyanin), juvenile plant growth habit, tillering, plant height, straw strength or lodging, flag leaf carriage at boot stage, leaf width and length, glaucosity of stems, leaves and spikes, pubescence of leaves and spikes, spike shape, spike density, spike awnedness, and plant color through-out stages of growth; plant growth characteristics, such as vernalization requirement, date for first stem joint emergence, heading date, flowering date, physiological maturity date and harvest maturity; tolerance to weather conditions, such as cold tolerance, resistance to heaving, tolerance to wet soils and standing water, drought and heat tolerance; and grain characteristics, such as grain yield, test weight, 1000 kernel weight, grain moisture, grain color, grain shape, grain protein, flour milling yield and baking characteristics.

During its development, wheat variety 6PASS54B was assayed and/or planted in field trials and evaluated for a variety of traits and/or characteristics as compared to check varieties. The property(s) of appropriate check varieties include but are not limited to varieties with a similar relative maturity, varieties known to be susceptible to one or more particular diseases, insect, pathogen, field condition, weather condition, soil type or condition, and/or crop management practice, varieties known to be tolerant or resistant to one or more particular diseases, insect, pathogen, field condition, weather condition, soil type or condition, and/or crop management practice, varieties comprising one or more particular marker locus, and/or varieties derived from another appropriate variety or having a particular pedigree. Appropriate choice of check varieties for comparison assures an appropriate baseline and valid qualitative or quantitative assessment of any test varieties.

In the development of 6PASS54B, the plants can be tested for various traits including, but not limited to grain yield, test weight, heading date, harvest maturity, plant height, straw strength, pre-harvest sprout tolerance, resistance levels to leaf rust, stripe rust, tan spot, *Septoria tritici* blotch, *Stagnospora nodorum* blotch, powdery mildew, *Fusarium* (scab), wheat yellow mosaic virus and soilborne mosaic virus, and grain characteristics such as flour yield, flour protein, and baking characteristics.

Wheat variety 6PASS54B, being substantially homozygous, can be reproduced by planting seeds of the line, growing the resulting wheat plants under self-pollinating or sib-pollinating conditions, and harvesting the resulting seed, using techniques familiar to the agricultural arts.

In one aspect, wheat plants, plant parts and seeds are provided which have all or essentially all of the characteristics set forth in Table 2. In one aspect, wheat plants, plant parts and seeds are provided which have all or essentially all of the physiological and morphological characteristics of wheat variety 6PASS54B, or all or essentially all of the phenotypic characteristics of wheat variety 6PASS54B, representative seed having been deposited as disclosed herein.

Wheat variety 6PASS54B can be further reproduced by tissue culture and regeneration. Tissue culture of various tissues of wheat and regeneration of plants therefrom is well known and widely published. Thus, in another aspect provided are cells which upon growth and differentiation produce wheat plants capable of having the physiological and morphological characteristics of wheat variety 6PASS54B.

As used herein, the term "plant parts" includes, without limitation, plant protoplasts, plant cell tissue cultures from which wheat plants can be regenerated, plant calli, plant clumps, plant cells, embryos, pollen, ovules, pericarp, seed, flowers, florets, heads, spikes, stems, stalks, leaves, roots, root tips, anthers, and the like. When indicating that a plant is crossed or selfed this indicates that any plant part of the plant can be used. For instance, the plant part does not need to be attached to the plant during the crossing or selfing, only the pollen might be used.

In one aspect, a wheat plant containing a locus conversion or an essentially derived variety of 6PASS54B is provided. Essentially derived varieties may be obtained, for example, by the selection of a natural or induced mutant, or of a somaclonal variant, the selection of a variant individual from plants of the initial variety, backcrossing, or transformation by genetic engineering, from the repeated use of variety 6PASS54B or being predominately derived from variety 6PASS54B.

A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single wheat variety.

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into wheat variety 6PASS54B.

In some examples, transgenic variants of wheat variety 6PASS54B are produced by introducing at least one transgene of interest into wheat variety 6PASS54B by transforming wheat variety 6PASS54B with a polynucleotide comprising the transgene of interest. In other examples, transgenic variants of wheat variety 6PASS54B are produced by introducing at least one transgene by introgressing the transgene into wheat variety 6PASS54B by crossing.

In one example, a process for modifying wheat variety 6PASS54B with the addition of a desired trait, said process comprising transforming a wheat plant of wheat variety 6PASS54B with a transgene that confers a desired trait is provided. In other examples, the genome of wheat variety 6PASS54B is transformed by genetic modification using techniques described herein, such as the CRISPR/Cas system adapted for use in plants. Therefore, transgenic wheat variety 6PASS54B cells, plants, plant parts, and seeds produced from this process are provided. In some examples one or more desired traits may include traits such as herbicide resistance, insect resistance, disease resistance, decreased phytate, modified fatty acid profile, modified fatty acid content, carbohydrate metabolism, protein content, or oil content.

Numerous methods for plant transformation are known in the art, including biological, such as the use of *Agrobacteria*, and physical, such as biolistic and particle bombardment, plant transformation protocols. In addition, expression vectors and in vitro culture methods for plant cell or tissue transformation and regeneration of plants such as those known in the art can be used.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genetic transformation such as genome editing or modification. As an example, a genetically modified plant variety can be generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1, incorporated herein by reference).

Plant transformation methods may involve the construction of an expression vector. Such a vector or recombinant construct comprises a DNA sequence that contains a coding sequence, such as a protein and/or RNA coding sequence under the control of or operatively linked to a regulatory element, for example a promoter. The vector or construct may contain one or more coding sequences and one or more regulatory elements.

A genetic trait which has been engineered into the genome of a particular wheat plant may then be moved into the genome of another variety using traditional breeding techniques that are well known in the plant breeding arts. For example, a backcrossing approach is commonly used to move a transgene from a transformed wheat variety into an elite wheat variety, and the resulting backcross conversion plant would then contain the transgene(s).

Various genetic elements can be introduced into the plant genome using transformation. These elements include, but are not limited to genes; coding sequences; inducible, constitutive, and tissue specific promoters; enhancing sequences; and signal and targeting sequences.

Provided are plants genetically engineered or transformed to express various phenotypes of agronomic interest. Expression of genes can be altered to enhance disease resistance, insect resistance, herbicide resistance, agronomic, grain quality, and other traits relative to a comparable wheat plant that does not contain the transformed element or to a comparable non-transformed plant. Transformation can also be used to insert DNA sequences which control or help control male-sterility. DNA sequences native to wheat as well as non-native DNA sequences can be transformed into the wheat plants described herein and used to alter levels of native or non-native proteins. Various promoters, targeting sequences, enhancing sequences, and other DNA sequences can be inserted into the genome for the purpose of altering the expression of proteins. Reduction or increase in the activity of specific genes by genetic transformation or modification can effect gene silencing, gene suppression or gene over expression in the plants described herein.

Many techniques for gene silencing are well known to one of skill in the art, including but not limited to, knock-outs, such as by insertion of a transposable element, antisense technology, (see U.S. Pat. Nos. 5,107,065; 5,453,566; and 5,759,829), co-suppression, RNA interference, virus-induced gene silencing, hairpin structures, ribozymes, oligonucleotide-mediated targeted modification (see, e.g., WO03/076574 and WO99/25853), Zn-finger targeted molecules (see, e.g., WO01/52620; WO03/048345; and WO00/42219), use of exogenously applied RNA (see, e.g., US20110296556), and other methods known to those of skill in the art or combinations of the above methods.

A genetic trait, engineered into a wheat plant using transformation techniques can be transferred into another line using traditional breeding techniques that are well known in the plant breeding arts. The wheat plants described herein can be the donor or the recipient of the transformed genetic trait. For example, a backcrossing approach can be used to move a transgene from a transformed wheat plant to an elite wheat variety to provide resulting progeny comprising a transgene. As used herein, "crossing" can refer to a simple X by Y cross, or the process of backcrossing, depending on the context. The term "breeding cross" excludes the processes of selfing or sibbing.

Transgenic or genetically modified wheat plants described herein can be harvested to produce a foreign or modified protein in commercial quantities. The foreign or modified protein can be extracted from a tissue of interest, such as a seed, or from total biomass by known methods. The approximate chromosomal location of the integrated or modified DNA molecule can be determined from a genetic map generated, for example, via conventional RFLP, PCR, and SSR analysis.

Particular markers used for these purposes may include any type of marker and marker profile which provides a means of distinguishing varieties. A genetic marker profile can be used, for example, to identify plants of the same variety or related varieties or to determine or validate a pedigree. In addition to being used for identification of wheat variety 6PASS54B and its plant parts, the genetic marker profile is also useful in developing a locus conversion of variety 6PASS54B.

Methods of isolating nucleic acids from wheat plants and methods for performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present. Methods for analyzing polynucleotides from plants, plant parts or seeds described herein may include contacting a polynucleotide from the plant, plant part or seed, such as from wheat variety 6PASS54B with a molecular marker or with modified nucleotides that facilitate sequencing of the polynucleotide. The polynucleotide may be isolated, separated or otherwise obtained from the plant, plant part or seed. Modified nucleotides such as dNTPs may be incorporated with the polynucleotides along with appropriate primers in a reaction mixture that facilitates sequencing. Sequencing can be done using any method known in the art.

A method comprising isolating nucleic acids, such as DNA, from a plant, a plant part, plant cell or a seed of the wheat varieties disclosed herein is provided. The method can include mechanical, electrical and/or chemical disruption of the plant, plant part, plant cell or seed, contacting the disrupted plant, plant part, plant cell or seed with a buffer or solvent, to produce a solution or suspension comprising nucleic acids, optionally contacting the nucleic acids with a precipitating agent to precipitate the nucleic acids, optionally extracting the nucleic acids, and optionally separating the nucleic acids such as by centrifugation or by binding to beads or a column, with subsequent elution, or a combination thereof. If DNA is being isolated, an RNase can be included in one or more of the method steps. The nucleic acids isolated can comprise all or substantially all of the genomic DNA sequence, all or substantially all of the chromosomal DNA sequence or all or substantially all of the coding sequences (cDNA) of the plant, plant part, or plant cell from which they were isolated. The nucleic acids isolated can comprise all, substantially all, or essentially all of the genetic complement of the plant. The nucleic acids isolated can comprise a genetic complement of the wheat variety. The amount and type of nucleic acids isolated may be sufficient to permit whole genome sequencing of the plant from which they were isolated or chromosomal marker analysis of the plant from which they were isolated.

The methods can be used to produce nucleic acids from the plant, plant part, seed or cell, which nucleic acids can be, for example, analyzed to produce data. The data can be recorded. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some examples, the nucleic acids produced can be sequenced or contacted with markers to produce a genetic profile, a molecular profile, a marker profile, a haplotype, or any combination thereof. In some examples, the genetic profile or nucleotide sequence is recorded on a computer readable medium. In other examples, the methods may further comprise using the nucleic acids produced from plants, plant parts, plant cells or seeds in a plant breeding program, for example in making crosses, selection and/or advancement decisions in a breeding program. Crossing includes any type of plant breeding crossing method, including but not limited to crosses to produce hybrids, outcrossing, selfing, backcrossing, locus conversion, introgression and the like.

Favorable genotypes and or marker profiles, optionally associated with a trait of interest, may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis. Variety 6PASS54B and its plant parts can be identified through a molecular marker profile. Such plant parts may be either diploid or haploid.

As described herein, genes or coding sequences can be expressed in transformed plants. More particularly, plants can be genetically engineered to express various phenotypes of agronomic interest. A single gene or locus conversion or at least about 1, 2, 3, 4, 5, 6, 7, 8, 9, 10, 11, 12, 13, 14, 15, 16, 17, 18, 19, 20, 25, 30, 35 or 40 or more genes or locus conversions and less than about 100, 90, 80, 70, 60, 50, 40, 30, 20, 15, or 10 genes or locus conversions may be introduced into a plant or comprised in the genome of the wheat plant. Combinations or stacks of two or more genes or coding sequences described herein can be used. Through the transformation of wheat, the expression of genes can be modulated to enhance disease resistance, insect resistance, herbicide resistance, water stress tolerance and agronomic traits as well as grain quality traits. These traits and the genes and organisms which may be targets are described in U.S. Pat. No. 8,809,554, which is incorporated herein by reference in its entirety for this purpose. Transformation can also be used to insert or modify DNA sequences which control or alter male-sterility. DNA sequences native to wheat can be modified as well as native and non-native DNA sequences can be introduced into wheat and used to modulate levels of native or non-native proteins. The sequences introduced can be heterologous comprising a coding sequence operably linked to a heterologous regulatory element, such as a promoter.

Exemplary genes which can be targeted include, but are not limited to, genes that confer resistance to pests such as Hessian fly, wheat stem sawfly, cereal leaf beetle, and/or green bug or disease, to pathogens *Cladosporium fulvum*, *Pseudomonas syringae*, *Fusarium graminearum* Schwabe, wheat rusts, *Septoria tritici*, *Septoria nodorum*, powdery mildew, *Helminthosporium* diseases, smuts, bunts, *Fusarium* diseases, bacterial diseases, and viral diseases.

Other genes, coding sequences or targets which can be used include those encoding *Bacillus thuringiensis* protein, a derivative thereof or a synthetic polypeptide modeled thereon. Examples of *Bacillus thuringiensis* transgenes encoding an endotoxin and being genetically engineered are given in the following patents and patent applications and hereby are incorporated by reference for this purpose: U.S. Pat. Nos. 5,188,960; 5,689,052; 5,880,275; 8,809,654; WO 91/14778; WO 99/31248; WO 01/12731; WO 99/24581; WO 97/40162 and U.S. application Ser. Nos. 10/032,717; 10/414,637; and 10/606,320.

Other genes, coding sequences or targets which can be used include those encoding an insect-specific hormone or pheromone such as an ecdysteroid and juvenile hormone, a variant thereof, a mimetic based thereon, or an antagonist or agonist thereof, an insect diuretic hormone receptor, such as an allostatin (see also U.S. Pat. No. 5,266,317 incorporated herein by reference for this purpose), an enzyme responsible for a hyper accumulation of a monoterpene, a sesquiterpene, a steroid, hydroxamic acid, a phenylpropanoid derivative or another non-protein molecule with insecticidal activity, an enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic; a molecule that stimulates signal transduction, for example mung bean calmodulin cDNA clones and maize calmodulin cDNA clones; a hydrophobic peptide (see U.S. Pat. Nos. 5,580,852 and 5,607,914 incorporated herein by reference for this purpose); a membrane permease, a channel former or a channel blocker, for example, cropin-beta lytic peptide analog conferring *Pseudomonas solanacearum*; an insect-specific antibody or an immunotoxin derived therefrom, or a virus-specific antibody; a developmental-arrestive protein such as a endopolygalacturonase-inhibiting protein or a ribosome-inactivating gene; genes involved in the Systemic Acquired Resistance (SAR) Response and/or the pathogenesis related genes, In some embodiments, coat protein-mediated resistance can be conferred in plants against one or more of alfalfa mosaic virus, cucumber mosaic virus, tobacco streak virus, potato virus X, potato virus Y, tobacco etch virus, tobacco rattle virus and tobacco mosaic virus. Such resistance may be conferred using, for example, a viral-invasive protein or a complex toxin derived therefrom.

In some embodiments, genes, coding sequences or targets which can be used include, without limitation, antifungal genes (see, for example, US Publication No: 20020166141 incorporated herein by reference for this purpose); detoxification genes, such as for fumonisin, beauvericin, moniliformin and zearalenone and their structurally related derivatives (see, for example, U.S. Pat. No. 5,792,931 incorporated herein by reference for this purpose); cystatin and cysteine proteinase inhibitors (see for example, US Patent Publication Serial No: 20050102717 incorporated herein by reference for this purpose), defensin genes (see for example, PCT Public WO03000863 and US Patent Publication Serial No: 20030041348); and genes conferring resistance to nematodes, see for example, WO 03/033651.

Genes, coding sequences, or targets that confer resistance to a herbicide are described, for example, in U.S. Pat. No. 8,809,654, which is incorporated by reference herein for this purpose. Examples include genes or coding sequences encoding acetohydroxy acid synthase, a chimeric protein of rat cytochrome P4507A1, yeast NADPH-cytochrome P450 oxidoreductase, glutathione reductase, superoxide dismutase, phosphotransferases, ALS and AHAS enzymes and other genes or coding sequences which confer resistance to a herbicide such as an imidazalinone or a sulfonylurea (see also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, each of which are incorporated herein by reference for this purpose); Glyphosate or glufosinate resistance can also be conferred using, for example, sequences encoding mutant 5-enolpyruvl-3-phosphikimate synthase (EPSP), aroA genes, phosphinothricin acetyl transferase (PAT), glyphosate oxido-reductase enzyme, glyphosate N-acetyltransferase, glutamine synthetase, *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. Nos. 4,769,061, 4,975,374, 4,940,835, 5,776,760, 5,463,175, 5,627,061, 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; US Patent Publication No. 20040082770 and international publications EP1173580; WO 01/66704; EP1173581 and EP1173582, EP 0 242 246 and EP 0 242 236, each of which are incorporated herein by reference for this purpose. See also, U.S. Pat. Nos. 5,969,213; 5,489,520; 5,550,318; 5,874,265; 5,919,675; 5,561,236; 5,648,477; 5,646,024; 6,177,616; and 5,879,903, each of which are incorporated herein by reference for this purpose.

Triazine resistance can be conferred using, for example, psbA and gs+ genes, sequences encoding a benzonitrile (nitrilase gene) such as disclosed in U.S. Pat. No. 4,810,648 incorporated herein by reference for this purpose.

Resistance to herbicides which target Protoporphyrinogen oxidase (protox) can also be conferred such resistance being described in U.S. Pat. Nos. 6,288,306, 6,282,837, 5,767,373 and international publication WO 01/12825 the disclosures of each of which are herein incorporated by reference for this purpose.

Genes, coding sequences, or targets that confer or improve grain quality include, without limitation, altered fatty acids (for example, oleic, linoleic, linolenic), altered phosphorus content (for example, using phytase), altered carbohydrates such as modulating the branching pattern of starch or altering thioredoxin, *Bacillus subtilis* levansucrase gene, *Bacillus licheniformis* alpha-amylase, tomato invertase, alpha-amylase gene, starch branching enzyme II, UDP-D-xylose 4-epimerase, Fragile 1 and 2, Ref1, HCHL, C4H, high oil seed such as by modification of starch levels (AGP). Fatty acid modification genes mentioned above may also be used to affect starch content and/or composition through the interrelationship of the starch and oil pathways, altered content or composition of antioxidants such as tocopherol or tocotrienols, such as using a phytl prenyl transferase (ppt), or through alteration of a homogentisate geranyl transferase (hggt). Genes, coding sequences, or targets that can be targets to confer or improve grain quality are disclosed in, for example, see U.S. Pat. Nos. 8,809,654, 6,787,683, 6,531,648, 6,423,886, 6,232,529, 6,197,561, 6,825,397, US Patent Publication Nos. 2003/0079247, US2003/0204870, US2004/0034886 international PCT publications WO 02/42424, WO 98/22604, WO 03/011015, WO02/057439, WO03/011015, WO 99/10498, WO 00/68393, and WO 03/082899.

Genes, coding sequences or targets for altered essential seed amino acids, such as one or more of lysine, methionine, threonine, tryptophan or altered sulfur amino acid content are also provided, can be used in the methods and plants described herein and are described in, for example, U.S. Pat. Nos. 8,809,654, 6,803,498, 6,127,600, 6,194,638, 6,346,403, 6,080,913, 5,990,389, 5,939,599, 5,912,414, 5,850,016, 5,885,802, 5,885,801, 5,633,436, 5,559,223, 6,664,445, 6,459,019, 6,194,638, 6,399,859, 6,441,274, international PCT applications WO99/40209, WO99/29882, WO98/20133, WO96/01905, WO98/56935, WO98/45458, WO98/42831, WO95/15392, WO01/79516, WO00/09706, and US Publication Nos. U52003/0150014, US2003/0163838, US2004/0068767, and US2004/0025203, the disclosures of each of which are herein incorporated by reference in their entirety for these purposes.

Genes, coding sequences or targets that control or alter male sterility and methods for conferring male sterility and male sterile plants are provided. There are several methods of conferring genetic male sterility available, such as disclosed in U.S. Pat. Nos. 8,809,654, 4,654,465 and 4,727,219, 3,861,709, 3,710,511, 5,432,068, the disclosures of each of which are herein incorporated by reference for this purpose. For additional examples of nuclear male and female sterility systems and genes, see also, U.S. Pat. Nos. 5,859,341; 6,297,426; 5,478,369; 5,824,524; 5,850,014; and 6,265,640; each of which are hereby incorporated by reference for this purpose.

Genes, coding sequences or targets that create a site for site specific DNA integration can also be used such as the introduction of FRT sites that may be used in the FLP/FRT system and/or Lox sites that may be used in the Cre/Loxp system. Other systems that may be used include the Gin recombinase of phage Mu, the Pin recombinase of *E. coli*, and the R/RS system of the pSR1 plasmid.

Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress are provided. For example, see: U.S. Pat. Nos. 8,809,654, 5,892,009, 5,965,705, 5,929,305, 5,891,859, 6,417,428, 6,664,446, 6,706,866, 6,717,034, 6,801,104, 6,177,275, 6,107,547, 6,084,153, US Patent Publication Nos. 2004/0148654, 2004/0237147, 2003/0166197, 2004/0128719, 2004/0098764, 2004/0078852, international PCT application WO2000060089, WO2001026459, WO2001035725, WO 00/73475; WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, WO01/36596 and WO9938977, WO2000/006341, WO04/090143, WO202776, WO2003052063, WO0164898, and WO200032761, the disclosures of each of which are herein incorporated by reference in its entirety for this purpose.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), and WO2004076638 and WO2004031349 (transcription factors), the disclosures of each of which are herein incorporated by reference.

Genes that confer agronomic enhancements, nutritional enhancements, or industrial enhancements can also be used. Such genes are described for example in U.S. Pat. No. 8,809,654, the disclosure of which is herein incorporated by reference in for this purpose. Such enhancements include, without limitation, improved tolerance to water stress from drought or high salt water condition. See e.g. U.S. Pat. Nos. 5,981,842, 5,780,709, international patent applications WO 92/19731, WO 92/19731 the disclosures of each of which is herein incorporated by reference for this purpose.

In some embodiments, methods of treating 6PASS54B with a mutagen and the plant produced by mutagenesis of 6PASS54B are provided. Backcross conversions of wheat variety 6PASS54B are also described. A backcross conversion occurs when modified or non-native DNA sequences are introduced through traditional (non-transformation) breeding techniques, such as backcrossing. DNA sequences, whether naturally occurring, modified or transgenes, may be introduced using these traditional breeding techniques. Desired traits transferred through this process include, but are not limited to, nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat by K. A. Lucken (pp. 444-452 In Wheat and Wheat Improvement, ed. Heyne, 1987). Examples of genes for other traits which can be used with the methods, plants and plant parts described herein include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtlD). The trait of interest is transferred from the donor parent to the recurrent parent, in this case, the wheat plant disclosed herein. Single gene traits, whether naturally occurring, induced by mutation or genetically altered, may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Methods of developing a backcross conversion 6PASS54B wheat plant are provided including the step of repeated backcrossing to wheat variety 6PASS54B. The number of backcrosses made may be 2, 3, 4, 5, 6, 7, 8 or greater, and fewer than 50, 40, 30, 25, 20, 15, 10, 9, or 8. The specific number of backcrosses used will depend upon the genetics of the donor parent and whether molecular markers are utilized in the backcrossing program. Provided are plants and plant populations that are produced from backcrossing methods, transformation, locus conversion, or otherwise produced, and combinations thereof and that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, or 99.9% or 99.95%, 99.98%, 99.985%, 99.99% or 99.995% of the genetic profile of wheat variety 6PASS54B. The percentage of the genetics retained in the backcross conversion may be measured by either pedigree analysis or through the use of genetic techniques such as molecular markers or electrophoresis. Such methods and techniques are described in U.S. Pat. No. 8,809,654, the disclosure of which is herein incorporated by reference for this purpose. The backcross conversion or locus conversion developed from this method may be similar to 6PASS54B for the results listed in Table 2. Such similarity may be measured by a side by side phenotypic comparison, with differences and similarities determined at a 5% significance level, when appropriate in environmental conditions that account for the trait being transferred. For example, herbicide should not be applied in the phenotypic comparison of herbicide resistant backcross conversion of 6PASS54B when compared back to 6PASS54B.

Described are methods for using wheat variety 6PASS54B in plant breeding and plants and plant populations produced by such methods. For example, wheat variety 6PASS54B can be crossed with another variety of wheat to form a first generation population of F1 plants. This first generation population of F1 plants will comprise an essentially complete set of the alleles of wheat variety 6PASS54B. Also provided are methods and plants which use transgenic or backcross conversions of wheat variety 6PASS54B to produce first generation F1 plants.

A method of developing a 6PASS54B-progeny wheat plant comprising crossing 6PASS54B with a second wheat plant and performing a breeding method is also described. An exemplary method for producing a line derived from wheat variety 6PASS54B is as follows. Wheat variety 6PASS54B is crossed with another variety of wheat, such as an elite variety. The F1 seed derived from this cross is grown to form a homogeneous population. The F1 seed contains one set of the alleles from variety 6PASS54B and one set of the alleles from the other wheat variety. The F1 genome is 50% variety 6PASS54B and 50% of the other elite variety. The F1 seed is grown and allowed to self, thereby forming F2 seed. On average the F2 seed would have derived 50% of its alleles from variety 6PASS54B and 50% from the other wheat variety, but various individual plants from the population can have a much greater percentage of their alleles derived from 6PASS54B. The F2 seed is grown and selection of plants made based on visual observation and/or measurement of traits. The 6PASS54B-derived progeny that exhibit one or more of the desired 6PASS54B-derived traits are selected and each plant is harvested separately. This F3 seed from each plant is grown in individual rows and allowed to self. Then selected rows or plants from the rows are harvested and threshed individually. The selections based on visual observation and/or measurements for desirable traits of the plants, such as one or more of the desirable 6PASS54B-derived traits are made. The process of growing and selection is repeated any number of times until a homozygous 6PASS54B-derived wheat plant is obtained. The homozygous 6PASS54B-derived wheat plant contains desirable traits derived from wheat variety 6PASS54B, some of which may not have been expressed by the other original wheat variety to which wheat variety 6PASS54B was crossed and some of which may have been expressed by both wheat varieties but now would be at a level equal to or greater than the level expressed in wheat variety 6PASS54B. The homozygous 6PASS54B-derived wheat plants have, on average, 50% of their genes derived from wheat variety 6PASS54B, but various individual plants from the population would have a much greater percentage of their alleles derived from 6PASS54B. The breeding process, of crossing, selfing, and selection may be repeated to produce another population of 6PASS54B-derived wheat plants with, on average, 25% of their genes derived from wheat variety 6PASS54B, and with various individual plants from the population having a much greater percentage of their alleles derived from 6PASS54B. Homozygous 6PASS54B-derived wheat plants that have received 6PASS54B-derived traits are also provided.

In some instances, selection may or may not occur at every selfing generation, selection may occur before or after the actual self-pollination process occurs, or individual selections may be made by harvesting individual spikes, plants, rows or plots at any point during the breeding process described herein. In addition, double haploid breeding methods may be used at any step in the process. In one aspect, the population of plants produced at each and any generation of selfing, each such population consisting of plants containing approximately 50% of its genes from wheat variety 6PASS54B, 25% of its genes from wheat variety 6PASS54B in the second cycle of crossing, selfing, and selection, 12.5% of its genes from wheat variety 6PASS54B in the third cycle of crossing, selfing, and selection, and so on.

Also disclosed are methods of obtaining a homozygous 6PASS54B-derived wheat plant by crossing wheat variety 6PASS54B with another variety of wheat and applying double haploid methods to the F1 seed or F1 plant or to any generation of 6PASS54B-derived wheat obtained by the selfing of this cross.

Still further, methods for producing 6PASS54B-derived wheat plants are provided by crossing wheat variety 6PASS54B with a wheat plant and growing the progeny seed and repeating the crossing or selfing along with the growing steps with the 6PASS54B-derived wheat plant from 1 to 2 times, 1 to 3 times, 1 to 4 times, or 1 to 5 times. Thus, any and all methods using wheat variety 6PASS54B in breeding, including selfing, pedigree breeding, backcrossing, hybrid production and crosses to populations are provided. Unique starch profiles, molecular marker profiles and/or breeding records can be used to identify the progeny lines or populations derived from these breeding methods.

Also disclosed are methods of harvesting the grain of variety wheat variety 6PASS54B and using the grain as seed for planting. Embodiments include cleaning the seed, treating the seed, and/or conditioning the seed. Cleaning the seed includes removing foreign debris such as weed seed and removing chaff, plant matter, from the seed. Conditioning the seed can include controlling the temperature and rate of dry down and storing seed in a controlled temperature environment. Seed treatment is the application of a composition to the seed such as a coating or powder. Seed material can be treated, typically surface treated, with a composition comprising combinations of chemical or biological herbicides, herbicide safeners, pesticides, insecticides, fungicides, nutrients, germination inhibitors, germination promoters, cytokinins, nutrients, plant growth regulators, antimicrobials, and activators, bactericides, nematicides, avicides, or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., published by the British Crop Production Council. Some specific seed treatments that may be used on crop seed include, but are not limited to, abscisic acid, acibenzolar-S-methyl, avermectin, amitrol, azaconazole, azospirillum, azoxystrobin, *bacillus, Bacillus subtilis, Bacillus simplex, Bacillus firmus, Bacillus amyloliquefaciens, Pasteuria* genus (e.g. *P. nishizawae*), bradyrhizobium, captan, carboxin, chitosan, clothianidin, copper, cyazypyr, difenoconazole, etidiazole, fipronil, fludioxonil, fluquinconazole, flurazole, fluxofenim, GB126, Harpin protein, imazalil, imidacloprid, ipconazole, isofavenoids, lipo-chitooligosaccharide, mancozeb, manganese, maneb, mefenoxam, metalaxyl, metconazole, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendaxole, thiamethoxam, thiocarb, thiram, tolclofos-methyl, triadimenol, trichoderma, trifloxystrobin, triticonazole and/or zinc.

Seed varieties and seeds with specific genetic resistance traits can be tested to determine which seed treatment options and application rates will complement such varieties and genetic resistance traits in order to enhance yield. For example, a variety with good yield potential but loose smut susceptibility will benefit from the use of a seed treatment that provides protection against loose smut. Likewise, a variety encompassing a genetic resistance trait conferring insect resistance will benefit from the second mode of action conferred by the seed treatment. Further, the good root establishment and early emergence that results from the proper use of a seed treatment will result in more efficient nitrogen use, a better ability to withstand drought and an overall increase in yield potential of a variety or varieties containing a certain trait when combined with a seed treatment.

The following assays can be used to characterize and/or select a wheat variety such as 6PASS54B during one or more stages of variety development. Other methods and assays are available and can be used in combination with or instead of the assays described herein.

Stripe Rust Screening.

Stripe rust is a fungal leaf disease that is most common in the mid-southern United States in the early spring. Significant levels of the disease can be found in some seasons anywhere in North America. The infection often mostly occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Leaf Rust Screening.

Leaf rust is a fungal leaf disease that is most common in the southern United States in the spring and early summer. Significant levels of the disease can be found in most seasons anywhere in North America. The infection is most damaging when it occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Leaf Blight Screening.

Fungal leaf blights, including Tan spot, *Septoria tritici* blotch, and *Stagnospora nodorum* blotch, are common in much of the North American wheat growing regions. The infection is most damaging when it occurs on the flag leaf but it may attack the entire plant, including the head. Natural infection of plants in the field may be rated visually using a 1-9 scale, where 1 indicates complete susceptibility and 9 indicates complete resistance.

Scab Screening.

*Fusarium* head blight or scab is a fungal disease that is common in much of the North American wheat growing regions. Infection occurs during flowering and is most severe when conditions are wet, warm and remain humid. The disease infects flowers on the spike and will spread to adjacent flowers, often infecting most of the developing kernels on the spike. Natural infection of plants in the field may be rated visually using a 1-9 scale, where 1 indicates complete susceptibility and 9 indicates complete resistance. Infection may be induced in controlled screening experiments where spikes are inoculated with specific spore concentrations of the fungus by spraying the spikes at flowering or injecting the inoculum directly into a flower on each spike. There are also molecular markers for QTL linked to some specific resistance genes.

Powdery Mildew Screening.

Powdery mildew is a fungal leaf disease that is most common in the southern United States in the spring and early summer. Significant levels of the disease can be found in many seasons anywhere in North America. The infection is most damaging when it occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Soilborne Mosaic Virus Screening.

Soilborne mosaic virus is transmitted by the vector, *Polymyxa graminis*, which tends to be most common in low-lying, wet soils; particularly those frequently grown to wheat. Symptoms appear in the spring as light green to yellow mottling along with stunting and resetting plant growth in the most susceptible varieties. Natural infection of plants in the field may be rated visually using a 1-9 scale, where 1 indicates complete susceptibility and 9 indicates complete resistance. Higher levels of natural infection can be induced for screening by planting wheat annually in the same field to increase the vector level.

Wheat Yellow (Spindle Streak) Mosaic Virus Screening.

Wheat yellow virus is transmitted by the vector, *Polymyxa graminis*, and is most common during cool weather conditions in the spring. Symptoms appear as light green to yellow streaks and dashes parallel to the leaf veins. Symptoms often fade prior to heading as weather conditions become warmer. Natural infection of plants in the field may be rated visually using a 1-9 scale, where 1 indicates complete susceptibility and 9 indicates complete resistance.

Flour Yield Screening.

The potential average flour yield of wheat can be determined on samples of grain that has been cleaned to standard and tempered to uniform moisture, using a test mill such as the Allis-Chalmers or Brabender mill. Samples are milled to established parameters, the flour sifted into fractions, which are then weighed to calculate flour yield as a percentage of grain weight.

Flour yield "as is" is calculated as the bran weight (over 40 weight) subtracted from the grain weight, divided by grain weight and times 100 to equal "as is" flour yield. Flour yield is calculated to a 15% grain moisture basis as follows: flour moisture is regressed to predict the grain moisture of the wheat when it went into the Quad Mill using the formula $$\text{Initial grain moisture} = 1.3429 \times (\text{flour moisture}) - 4.$$

The flour yields are corrected back to 15% grain moisture after estimating the initial grain moisture using the formula $$\text{Flour Yield}_{(15\%)} = \text{Flour Yield}_{(as\ is)} - 1.61\% \times (15\% - \text{Actual flour moisture})$$

Flour Protein Screening.

The protein content as a percentage of total flour may be estimated by the Kjeldahl method or properly calibrated near-infrared reflectance instruments to determine the total nitrogen content of the flour.

Flour protein differences among cultivars can be a reliable indicator of genetic variation provided the varieties are grown together, but can vary from year to year at any given location. Flour protein from a single, non-composite sample may not be representative. Based on the Soft Wheat Quality Laboratory grow-outs, protein can vary as much 1.5% for a cultivar grown at various locations in the same ½ acre field.

Sucrose Solvent Retention Capacity (SRC).

The solvent retention capacity (SRC) of wheat flour measures the ability of the flour to retain various solvents after centrifugation. Sucrose SRC predicts the starch damage and pentosan components, and can be correlated to sugar-snap cookie diameter quality metrics.

Sucrose SRC is a measure of arabinoxylans (also known as pentosans) content, which can strongly affect water absorption in baked products. Water soluble arabinoxylans are thought to be the fraction that most greatly increases sucrose SRC. Sucrose SRC a predictor of cookie quality, with sugar snap cookie diameters decreasing by 0.07 cm for each percentage point increase in sucrose SRC. The negative correlation between wire-cut cookie and sucrose SRC values is $r=-0.66$ ($p<0.0001$). Sucrose SRC typically increases in wheat samples with lower flour yield ($r=-0.31$) and lower softness equivalent ($r=-0.23$). The cross hydration of gliadins by sucrose also causes sucrose SRC values to be correlated to flour protein ($r=0.52$) and lactic acid SRC ($r=0.62$). Soft wheat flours for cookies typically have a target of 95% or less when used by the US baking industry for biscuits and crackers. Sucrose SRC values increase by 1% for every 5% increase in lactic acid SRC. The 95% target value can be exceeded in flour samples where a higher lactic acid SRC is required for product manufacture since the higher sucrose SRC is due to gluten hydration and not to swelling of the water soluble arabinoxylans.

Lactic Acid SRC

Lactic Acid SRC=Lactic Acid Solvent Retention Capacity. Lactic acid SRC measures gluten strength. Typical values are below 85% for "weak" soft varieties and above 105% or 110% for "strong" gluten soft varieties. See the above discussion of protein quality in this section for additional details of the lactic acid SRC. Lactic acid SRC results correlate to the SDS-sedimentation test. The lactic acid SRC is also correlated to flour protein concentration, but the effect is dependent on genotypes and growing conditions. The SWQL typically reports a protein-corrected lactic acid SRC value to remove some of the inherent protein fluctuation not due to cultivar genetics. Lactic acid is corrected to 9% protein using the assumption of a 7% increase in lactic acid SRC for every 1% increase in flour protein. On average across 2007 and 2008, the change in lactic acid SRC value was closer to 2% for every 1% protein.

Molecular Sreening

Plants are analyzed at various times throughout the development of 6PASS54B for specific alleles for scab resistance. As discussed above, and as is known to those skilled in the art, other traits can also be screened by molecular analysis.

A description of the traits used to measure or characterize a wheat variety such as variety 6PASS54B and the scoring ranges used for such traits are described below in Table 1.

TABLE 1

Description of traits and scores used.

| TRAIT | DESCRIPTION & HOW SCORED |
|---|---|
| HD DAT | Heading Date in days past Jan. 1st); plot dated on the day when approximately 50% of the heads are 50% out of the boot |
| HGTIN HGTCM | Height (inches or centimeters); scored with a measuring stick after all genotypes fully extended; wheat gathered around stick and average distance to the top of the heads is noted; 2-3 samplings per plot |
| LF BLT | Leaf Blight Complex; score based on amount of infection on flag and flag −1 leaves; typical scale: |

| | % of uninfected leaf surface area | |
|---|---|---|
| | flag | flag −1 |
| 9- | 100% | 100% |
| 8- | 100% | 75% |
| 7- | 100% | 50% |
| 6- | >90% | <50% |
| 5- | 75-90% | <25% |
| 4- | 50-74% | — |
| 3- | 23-49% | — |
| 2- | 10-24% | — |
| 1- | 0-9% | — |

| TRAIT | DESCRIPTION & HOW SCORED |
|---|---|
| LF RST | Leaf Rust; score based on amount of infection evident on flag leaves; typical scale:<br>9- clean<br>8- trace amounts<br>7- <5% flag leaf area infected<br>6- 6-10% flag leaf area infected<br>5- 11-20% flag leaf area infected<br>4- 21-30% flag leaf area infected<br>3- 31-40% flag leaf area infected<br>2- 41-50% flag leaf area infected<br>1- over 50% flag leaf area infected |

TABLE 1-continued

Description of traits and scores used.

| TRAIT | DESCRIPTION & HOW SCORED |
|---|---|
| MAT | Maturity; used on larger, earlier generation tests in the place of heading date; scale based on maturity of known checks and will vary from year to year based on when the note is taken; typical scale:<br>9- very late, boot not swelling when note is taken<br>8- still in boot when note is taken<br>7- splitting boot, will head two days after note is taken<br>6- will head day after the note is taken<br>5- headed on the day note is taken<br>4- headed day before note taken<br>3- headed two days before note taken<br>2- fully extended, some flowering visible<br>1- extended and flowering<br>Maturity may also be scored at physiological maturity; typical scaler:<br>9- ready to be harvested<br>7- caryopse hard to divide<br>5- head yellowing on day note is taken<br>3- grain still at dough stage<br>1- head completely green |
| PM | Powdery Mildew; score based on severity of infection and progression of the disease up the plant; scale based on reaction of known checks with attention given to race changes; typical scale:<br>9- clean<br>8- trace amount low on plants<br>7- slight infection mostly low on plants<br>6- moderate infection low on plants; trace amounts on flag −1 leaves<br>5- moderate infection low on plants, moderate amounts on flag −1 leaves<br>4- moderate infection through canopy with trace amounts evident on flag leaves<br>3- severe infection through canopy with up to 25% infection on flag leaves<br>2- severe infection through canopy with up to 50% infection on flag leaves<br>1- severe infection; greater than 50% infection on flag leaves |
| SB MV | Soil Borne Mosaic Virus; score based on amount of mottling, chlorosis, and/or stunting; scale based on reaction of known checks; typical scale<br>1- severe stunting to the point of rosettes<br>2- severe stunting<br>3- very chlorotic with moderate stunting<br>4- very chlorotic with mild stunting<br>5- moderate mottling with no stunting<br>6- mottling evident<br>7- mottling barely visible<br>8- green, very little mottling<br>9- green, no mottling visible |
| SHTSC | Shattering score. Scores are based on the amount of grain that is visible in the spike just before harvest.<br>9- grain no visible in the spike, Glumes closed.<br>8- Glumes slightly opened in <10% of the grains.<br>7- Glumes slightly opened in >10% of the grains.<br>6- Glumes moderately opened in <20% of the grains.<br>5- Glumes moderately opened in >20% of the grains.<br>4- Glumes completely opened in <30% of the grains.<br>3- Glumes completely opened in >30% of the grains.<br>2- 20%-50% of the grain on the soil<br>1- >50% of the grain on the soil. |
| SS MV | Spindle Streak Mosaic Virus; score based on amount of mottling and chlorosis; scale based on reaction of known checks; scale similar to SS MV with less emphasis on stunting |
| ST EDG | Straw Lodging; score based on amount of lodging; typical scale:<br>9- still upright<br>8- only slight leaning<br>7- some leaning, no lodging<br>6- moderate leaning, little lodging<br>5- up to 10% lodged<br>4- 11-25% lodged<br>3- 26-50% lodged<br>2- 51-75% lodged<br>1- greater than 75% lodged |

TABLE 1-continued

Description of traits and scores used.

| TRAIT | DESCRIPTION & HOW SCORED |
|---|---|
| STPRST | Stripe rust. Stripe rust is an important disease that occurs most often in Europe. The infection may only affect the flag leaf, or it may attack the entire plant including the head. Two scales based on level of infection included below:<br>Score based on the amount of infection of the whole plant!<br>9- clean<br>8- traces<br>7- <5% plant infected<br>6- 10% plant infected<br>5- 20% plant infected<br>4- 40% plant infected<br>3- 60% plant infected<br>2- 60% plant infected head rusted<br>1- Plant not able to produce kernel<br>Score based on the amount and type of infection evident on flag leaves:<br>9- clean<br>8- trace amounts (Chlorotic-necrotic freckles)<br>7- <5% flag leaf area infected<br>6- 6-10% flag leaf area infected (chlorotic-necrotic stripes).<br>5- 11-20% flag leaf area infected (chlorotic-necrotic stripes).<br>4- 21-30% flag leaf area infected (chlorotic-necrotic stripes).<br>3- 31-40% flag leaf area infected (chlorotic-necrotic stripes).<br>2- 41-50% flag leaf area infected (some chlorosis).<br>1- over 50% flag leaf area infected (no chlorosis). |
| UNI | Uniformity; used to determine how pure a line is generally at the F7 (pre-advanced) generation; typical scale:<br>9- very uniform in all aspects<br>8- good uniformity<br>7- fairly uniform, but some off-types<br>6- several off-types, but can be cleaned up with normal purification procedures<br>5- several off-types, will be a challenge to clean up with normal purification procedures<br>4- considerable number of off-types; will need to be reselected to proceed as a pureline<br>3- as many as 25% off types; will need to be reselected<br>2- as many as 50% off types; will need to be reselected<br>1- more than 50% off types; what you have here is a problem |
| WNTHRD | Winter Hardiness; score based on amount of brownback and kill; best scored at time of early spring regrowth; typical scale:<br>9- very green, no brown-back<br>8- green, slight brown-back<br>7- moderate brown-back<br>6- hard brown-back, no kill<br>5- hard brown-back with less than 10% kill<br>4- 11-25% kill<br>3- 26-50% kill<br>2- 51-75% kill<br>1- greater than 75% kill |
| SC AB | Fusarium head scab; score based on visual evaluation of the percentage of scab infected heads on a whole plot basis with consideration given to both total heads affected and severity of infection; typical scale:<br>9- no scab infection<br>8- trace amount (1-2%) with infections limited to individual spikelets<br>7- up to 5% infection with most infection limited to less than 50% of the spike<br>6- 5-15% of heads infected<br>5- 15-30% of heads infected<br>4- 30-50% of heads infected<br>3- 50-75% of heads infected<br>2- 75-90% of heads infected<br>1- >90% of heads infected<br>most genotypes scoring 5 or below would typically have the majority of the spike infected |

It will be apparent to those of skill in the art that variations may be applied to the compositions and methods described herein and in the steps or in the sequence of steps of the method described herein without departing from the concept, spirit and scope of the invention. More specifically, it will be apparent that certain changes and modifications such as single gene conversions, including for example, modifications and mutations, somoclonal variants, variant individuals selected from large populations of the plants of the instant variety and the like may be practiced. All such similar substitutes and modifications apparent to those skilled in the art are deemed to be within the spirit, scope and concept of the invention.

It is to be understood that the invention is not limited in its application to the details of components set forth in the description. Also, the phraseology and terminology used herein is for the purpose of description and should not be regarded as limiting. The use of "including," "comprising," or "having" and variations thereof herein encompasses the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications are herein expressly incorporated by reference in their entirety for all purposes to the same extent as if each individual publication or patent application was specifically and individually incorporated by reference. In case of conflict between the present disclosure and the incorporated patents, publications and references, the present disclosure should control.

DEPOSIT

Applicant has made a deposit of at least 625 seeds of wheat line variety 6PASS54B with the National Center for Marine Algae and Microbiota (NCMA), 60 Bigelow Drive, East Boothbay, ME 04544, USA, with NCMA Deposit No. 202110038. The seeds deposited with the NCMA on Oct. 12, 2021 are from the seed stock maintained by Pioneer Hi-Bred International, Inc., 7250 NW $62^{nd}$ Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon issuance of any claims in the application, the Applicant will make the deposit available to the public pursuant to 37 C.F.R. § 1.808. This deposit of the Wheat line 6PASS54B will be maintained in the NCMA depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.). Unauthorized seed multiplication is prohibited.

Example 1: Breeding History of Wheat Line Variety 6PASS54B

Wheat line 6PASS54B was developed by from a cross between three homozygous lines and comprises: 25% of 25R34, 25% of proprietary wheat variety 6PBCC85B that has not been publicly disclosed and 50% of XW10S. Wheat line 6PASS54B, being substantially homozygous, can be reproduced by planting seeds of the line, growing the resulting wheat plants under self-pollinating or sib-pollinating conditions, and harvesting the resulting seed, using techniques familiar to the agricultural arts.

Line 6PASS54B was bred and selected using a modified pedigree selection method for any and all of the following characteristics in the field environment: disease resistance, plant type, plant height, head type, straw strength, maturity, grain yield, test weight, and milling and baking characteristics.

Line 6PASS54B has shown no variants other than what would normally be expected due to environment.

Example 2: Traits and Characteristics of 6PASS54B

TABLE 2

| VARIETY DESCRIPTION INFORMATION 6PASS54B | |
| --- | --- |
| | 6PASS54B |
| 1. Kind | |
| 1= common 2=Durum 3=Club 4=Other | 1 |
| 1a. Common Wheat Market Classes HRW, HRS, HW, SRW, SW | SRW |
| 2. VERNALIZATION | |
| 1 = Spring 2 = Winter 3 = Other | 2 |
| 3. COLEOPTILE ANTHOCYANIN | |
| 1 = Absent 2 = Present | 1 |
| 4. JUVENILE PLANT GROWTH | |
| 1 = Prostrate 2 = Semi-Erect 3 = Erect | 2 |
| 5. PLANT COLOR | |
| 1 = Yellow-Green 2 = Green 3 = Blue-Green | 2 |
| 6. FLAG LEAF | |
| 1 = Erect 2 = Recurved | 1 |
| 1 = Not Twisted 2 = Twisted | 2 |
| 1 = Wax Absent 2 = Wax Present | 2 |
| 7. EAR EMERGENCE | |
| Number of Days (Average) | 137 |
| Number of Days Same As | |
| Number of Days Later Than | |
| Number of Days Earlier Than 25R40 | 3 |
| 8. ANTHER COLOR | |
| 1 = Yellow 2 = Purple | 1 |
| 9. PLANT HEIGHT | |
| cm (Average) | 93 |
| cm Taller than 25R40 | 5 |
| cm Shorter than | |
| 10. STEM | |
| ANTHOCYANIN 1 = Absent 2 = Present | 2 |
| WAXY BLOOM 1 = Absent 2 = Present | 2 |
| HAIRINESS (last internode of rachis) 1 = Absent 2 = Present | 2 |

TABLE 2-continued

| VARIETY DESCRIPTION INFORMATION 6PASS54B | |
| --- | --- |
| | 6PASS54B |
| INTERNODE 1 = Hollow 2 = Semi-Solid 3 = Solid | 1 |
| PEDUNCLE 1 = Erect 2 = Recurved 3 = Semi-Erect | 3 |
| AURICLE Anthocyanin: 1 = Absent 2 = Present | 2 |
| AURICLE Hair: 1 = Absent 2 = Present | 2 |
| 11. HEAD | |
| DENSITY 1 = Lax 2 = Middense (Laxidense) 3 = Dense | 2 |
| SHAPE 1 = Tapering 2 = Strap 3 = Clavate 4 = Other (Specify) | 1 |
| CURVATURE 1 = Erect 2 = Inclined 3 = Recurved | 2 |
| AWNEDNESS 1 = Awnless 2 = Apically Awnletted 3 = Awnletted 4 = Awned | 4 |
| 12. GLUMES | |
| COLOR 1 = White 2 = Tan 3 = Other (Specify) | 2 |
| SHOULDER 1 = Wanting 2 = Oblique 3 = Rounded 4 = Square 5 = Elevated 6 = Apiculate 7 = Other (Specify) | 2 |
| SHOULDER WIDTH 1 = Narrow 2 = Medium 3 = Wide | 2 |
| BEAK SHAPE 1 = Obtuse 2 = Acute 3 = Acuminate | 1 |
| BEAK WIDTH 1 = Narrow 2 = Medium 3 = Wide | 2 |
| GLUME LENGTH 1 = Short (ca. 7 mm) 2 = Medium (ca. 8 mm) 3 = Long (ca. 9 mm) | 2 |
| WIDTH 1 = Narrow (ca. 3 mm) 2 = Medium (ca. 3.5 mm) 3 = Wide (ca. 4 mm) | 2 |
| PUBESCENCE 1 = Not Present 2 = Present | 1 |
| 13. SEED | |
| SHAPE 1 = Ovate 2 = Oval 3 = Elliptical | 1 |
| CHEEK SHAPE 1 = Rounded 2 = Angular | 1 |
| BRUSH SIZE 1 = Short 2 = Medium 3 = Long | 1 |
| BRUSH 1 = Not Collared 2 = Collared | 1 |
| CREASE 1 = Width 60% or less of Kernel 2 = Width 80% or less of Kernel 3 = Width Nearly as Wide as Kernel | 2 |
| CREASE 1 = Depth 20% or less of Kernel 2 = Depth 35% or less of Kernel 3 = Depth 50% or less of Kernel | 2 |
| COLOR 1 = White 2 = Amber 3 = Red 4 = Other (Specify) | 3 |
| TEXTURE 1 = Hard 2 = Soft 3 = Other (Specify) | 2 |
| PHENOL REACTION 1 = Ivory 2 = Fawn 3 = Light Brown 4 = Dark Brown 5 = Black | 4 |
| SEED WEIGHT g/1000 Seed (Whole Number Only) | 34 |
| GERM SIZE 1 = Small 2 = Midsize 3 = Large | 2 |
| 14. RACE (0 = Not Tested 1 = Susceptible 2 = Resistant 3 = Intermediate 4 = Tolerant) "Field races" unless specified | 0 |
| Stem Rust (*Puccinia graminis* f. sp. *tritici*) | 0 |
| Leaf Rust (*Puccinia recondita* f. sp. *tritici*) | 3 |
| Stripe Rust (*Puccinia striiformis*) | 2 |
| Loose Smut (*Ustilago tritici*) | 0 |
| Powdery Mildew (*Erysiphe graminis* f. sp. *tritici*) | 0 |
| Common Bunt (*Tilletia tritici* or *T. laevis*) | 0 |
| Dwarf Bunt (*Tilletia controversa*) | 0 |
| Karnal Bunt (*Tilletia indica*) | 0 |
| Flag Smut (*Urocystis agropyri*) | 0 |
| Tan Spot (*Pyrenophora tritici-repentis*) | 0 |
| Halo Spot (*Selenophoma donacis*) | 0 |
| *Septoria* spp. | 0 |
| *Septoria nodorum* (Glume Blotch) | 0 |
| *Septoria avenae* (Speckled Leaf Disease) | 0 |
| *Septoria tritici* (Speckled Leaf Blotch) | 0 |
| Scab (*Fusarium* spp.) | 3 |
| "Snow Molds" | 0 |
| Kernel Smudge ("Black Point") | 0 |
| Common Root Rot (*Fusarium, Cochliobolus* and *Bipolaris* spp.) | 0 |
| Barley Yellow Dwarf Virus (BYDV) | 0 |
| Rhizoctonia Root Rot (*Rhizoctonia solani*) | 0 |
| Soilborne Mosaic Virus (SBMV) | 2 |
| Black Chaff (*Xanthomonas campestris* pv. *translucens*). | 0 |
| Wheat Yellow (Spindle Streak) Mosaic Virus | 2 |
| Bacterial Leaf Blight (*Pseudomonas syringae* pv. *syringae*) | 0 |
| Wheat Streak Mosaic Virus (WSMV) | 0 |

What is claimed is:

1. A plant, plant part, seed, or plant cell of wheat line 6PASS54B, representative seed of said wheat line 6PASS54B having been deposited under NCMA accession number 202110038.

2. An F1 wheat seed produced from (i) selfing the plant or plant part of claim 1 or (ii) a single crossing of the plant or plant part of claim 1 with a different wheat plant or plant part.

3. A wheat plant or plant part produced by growing the wheat seed of claim 2.

4. The wheat seed of claim 2, wherein the seed is an F1 hybrid wheat seed.

5. A method for producing a progeny seed, the method comprising crossing the wheat plant of claim 3, to a plant of wheat line 6PASS54B, representative seed of said wheat line 6PASS54B having been deposited under NCMA accession number 202110038 and producing a progeny seed.

6. The method of claim 5, wherein the method further comprises crossing a plant grown from the progeny seed to a plant of wheat line 6PASS54B and producing a back-crossed seed.

7. A method for producing a second wheat plant, the method comprising applying plant breeding techniques to the wheat plant or plant part of claim 3, wherein application of said techniques results in the production of a second wheat plant.

8. A method for producing a second wheat plant, the method comprising doubling haploid seed generated from a cross of the wheat plant or plant part of claim 3 with a different wheat plant.

9. A method comprising cleaning the seed of claim 1.

10. The seed of claim 1, further comprising a seed treatment on the surface of the seed.

11. A method for producing nucleic acids, the method comprising isolating nucleic acids from the plant, plant part, seed, or plant cell of claim 1.

12. A method of producing a wheat plant comprising a locus conversion, the method comprising introducing a locus conversion into wheat line 6PASS54B, wherein the locus conversion was introduced by backcrossing or genetic transformation into wheat line 6PASS54B and wherein a sample of wheat line 6PASS54B has been deposited under NCMA Accession No. 202110038.

13. The method of claim 12, wherein the locus conversion comprises a transgene.

14. A plant, plant part, seed, or plant cell of wheat line 6PASS54B, representative seed of said wheat line 6PASS54B having been deposited under NCMA accession number 202110038, further comprising a single locus conversion, wherein the plant or a plant grown the seed, plant part or plant cell comprises the a single locus conversion and otherwise comprises all of the physiological and morphological characteristics of wheat line 6PASS54B when grown under the same environmental conditions.

15. The plant, plant part, seed, or plant cell of claim 14, wherein the a single locus conversion confers a trait selected from the group consisting of male sterility, abiotic stress tolerance, altered phosphate content, altered protein, altered antioxidants, altered fatty acids, altered essential amino acids, altered carbohydrates, herbicide resistance, insect resistance and disease resistance, wherein the altered trait is compared with a similar plant not comprising the locus conversion.

16. A tissue culture produced from the plant, plant part, seed, or plant cell of claim 14.

17. A wheat seed produced by crossing the plant of claim 14 with a different wheat plant.

18. A wheat plant produced by growing the wheat seed of claim 17.

19. A method for producing a second wheat plant, the method comprising applying plant breeding techniques to the wheat plant of claim 18, wherein application of said techniques results in the production of a second wheat plant.

20. A method for producing nucleic acids, the method comprising isolating nucleic acids from the seed, plant, plant part, or plant cell of claim 14.

* * * * *